US012091444B2

(12) United States Patent
Arora et al.

(10) Patent No.: US 12,091,444 B2
(45) Date of Patent: Sep. 17, 2024

(54) INTRADERMAL ADMINISTRATION OF IMMUNOGLOBULIN G PREPARATION

(71) Applicant: GRIFOLS WORLDWIDE OPERATIONS LIMITED, Dublin (IE)

(72) Inventors: Vikram Arora, Raleigh, NC (US); Ralph Christian Crumrine, Durham, NC (US); Kristine Bergstrand, Chapel Hill, NC (US); Hongbin Li, Morrisville, NC (US); Todd W. Willis, Cary, NC (US)

(73) Assignee: Grifols Worldwide Operations Limited, Dublin (IE)

( * ) Notice: Subject to any disclaimer, the term of this patent is extended or adjusted under 35 U.S.C. 154(b) by 666 days.

(21) Appl. No.: 16/805,425

(22) Filed: Feb. 28, 2020

(65) Prior Publication Data

US 2020/0199201 A1 Jun. 25, 2020

Related U.S. Application Data

(63) Continuation of application No. 15/407,139, filed on Jan. 16, 2017, now abandoned.

(60) Provisional application No. 62/292,075, filed on Feb. 5, 2016.

(51) Int. Cl.

| | |
|---|---|
| ***A61P 37/00*** | (2006.01) |
| ***A61K 9/00*** | (2006.01) |
| ***A61K 39/00*** | (2006.01) |
| ***A61M 37/00*** | (2006.01) |
| ***C07K 16/00*** | (2006.01) |

(52) U.S. Cl.

CPC ............ *C07K 16/00* (2013.01); *A61K 9/0021* (2013.01); *A61K 39/00* (2013.01); *A61M 37/00* (2013.01); *A61K 2039/505* (2013.01); *A61K 2039/54* (2013.01)

(58) Field of Classification Search

None

See application file for complete search history.

(56) References Cited

U.S. PATENT DOCUMENTS

| | | | |
|---|---|---|---|
| 7,754,208 | B2 | 7/2010 | Ledbetter et al. |
| 9,926,362 | B2 | 3/2018 | Strome |
| 2005/0196380 | A1 | 9/2005 | Mikszta et al. |

FOREIGN PATENT DOCUMENTS

| | | | | |
|---|---|---|---|---|
| EP | 2 271 363 | A1 | 1/2011 | |
| JP | 2014-514345 | A | 6/2014 | |
| WO | WO-2005023328 | A2 * | 3/2005 | ........... A61K 9/0019 |
| WO | WO 2005/086773 | A2 | 9/2005 | |
| WO | WO 2005/086773 | A3 | 9/2005 | |
| WO | WO 2008/151088 | A2 | 12/2008 | |
| WO | WO 2009/117085 | A1 | 9/2009 | |
| WO | WO 2012/151199 | A1 | 11/2012 | |
| WO | WO 2014/143909 | A1 | 9/2014 | |
| WO | WO 2016/161423 | A1 | 10/2016 | |

OTHER PUBLICATIONS

Kahwaji, Clin J Am Soc Nephrol 4: 1993-1997, 2009. (Year: 2009).*

Zulfikar et al., Türk Ped Arş 2014; 49: 282-8. (Year: 2014).*

Tabers Cyclopedic Medical Dictionary, 1993, pp. 1012-1013. (Year: 1993).*

Vivaglobin Immune Globulin Subcutaneous, highlights of prescribing information, pp. 1-8, 2010. (Year: 2010).*

Harvey et al. Pharm Res (2011) 28:107-116. (Year: 2011).*

Haraoui et al., Therapeutics and Clinical Risk Management 2007:3(1) 99-10. (Year: 2007).*

Kaymakcalan et al. (Clinical Immunology (2009) 131, 308-316). (Year: 2009).*

Gustafson, R., et al., Rapid subcutaneous immunoglobulin administration every second week results in high and stable serum immunoglobulin G levels in patients with primary antibody deficiencies, Clinical and Experimental Immunology, vol. 152, No. 2, pp. 274-279, 2008.

Patent Search Report, dated May 19, 2020, in Russian Application 2017100665/14.

Schiff, R.I., Half-Life And Clearance of pH 6.8 and pH 4.25 Immunoglobulin G Intravenous Preparations In Patients With Primary Disorders Of Humoral Immunity, Reviews Of Infectious Diseases, vol. 8, Issue Supplement 4, pp. S449-S456, 1986.

Examination Report dated Sep. 24, 2021 in Indian Application No. 201744000094, in 5 pages.

Gardulf, et al., Rapid Subcutaneous IgG Replacement Therapy is Effective and Safe in Children and Adults with Primary Immunodeficiencies—A Prospective, Multi-National Study, Journal of Clinical Immunology, vol. 26, No. 2, pp. 177-185, 2006.

Office Action dated Dec. 31, 2021 in Chinese Application No. 2017100181068, in 12 pages.

Barbara Torrisi Thesis 2012, "Liquid loaded microneedles for the intradermal delivery of botulinum toxin for Primary Focal Hyperhidrosis," pp. 1-245. (Year: 2012).

Burton, S.A., et al., Rapid Intradermal Delivery of Liquid Formulations Using a Hollow Microstructured Array, Pharmaceutical Research, vol. 28, No. 1, pp. 31-40, Jun. 26, 2010.

Desai et al. (J Allergy Clin Immunol. Oct. 2009; 124(4):854-6). (Year: 2009).

Froehlich et al. (CID, 2001 :33, 906-908). (Year: 2001).

Gammagard S/D, Immune Globulin Intravenous (Human), pp. 1-24, 2014. (Year: 2014).

Gardulf et al. (Journal of Clinical Immunology, vol. 26, No. 2, Mar. 2006). (Year: 2006).

Gupta et al. (Diabetes Technol Ther. Apr. 2011; 13(4):451-6). (Year: 2011).

(Continued)

*Primary Examiner* — Zachary S Skelding

(74) *Attorney, Agent, or Firm* — Knobbe, Martens, Olson & Bear

(57) ABSTRACT

A method for administration of an IgG preparation by an intradermal (ID) route to a subject includes loading with a volume of the IgG preparation an ID delivery device including needles, applying the device to a skin delivery site, using the device to allow dermal penetration of the needles, delivering the volume of the IgG preparation at the skin delivery site, and removing the injection delivery device. The method can be used in the treatment of a disease, such as an immunodeficiency.

4 Claims, 2 Drawing Sheets

(56) References Cited

OTHER PUBLICATIONS

Jolles et al., "Current treatment options with immunoglobulin G for the individualization of care in patients with primary immunodeficiency disease", Clinical and Experimental Immunology, 179: 146-160, 2014.
Kobrynski, "Subcutaneous immunoglobulin therapy:new option for patients with primary immunodeficiency diseases" Biologics: Targets and Therapy, 2012:277-287. (Year: 2012).
Korkmaz, E., et al., Therapeutic intradermal delivery of tumor necrosis factor-alpha antibodies using tip-loaded dissolvable microneedle arrays, Acta Biomaterialia, vol. 24, pp. 96-105, Jun. 18, 2016.
Kuriakose, A., et al., Immunogenicity of Biotherapeutics: Causes and Association with Posttranslational Modifications, Journal of Immunology Research, vol. 2016, Article ID 1298473, PMID 27437405, 18 pages, 2016.
Lisa Dick ("Pointing the Way," Innovations in Pharmaceutical Technology issue 50. © Samedan Ltd. 2014, pp. 1-3) (Year: 2014).
Monkare, J., et al., IgG-loaded hyaluronan-based dissolving microneedles for intradermal protein delivery, Journal of Controlled Release, vol. 218, pp. 53-62, Oct. 5, 2015.
Nanopass micronjet 600 FDA approval 2010, pp. 1-5 as renumbered by the Examiner. (Year: 2010).
Parmley et al. (SciBX 7(39), 2015, pp. 1-3). (Year: 2015).
Product information for AusPAR Hizentra Normal Human Immunoglobulin CSL Behring Ltd 2013-00301-2-2 Final Jun. 25, 2014, pp. 1-15. (Year: 2014).
Torrisi, B., Thesis 2012, Liquid Loaded Microneedles for the Intradermal Delivery of Botulinum Toxin for Primary Focal Hyperhidrosis, pp. 1-245, 2012.
Extended European Search Report, dated Apr. 4, 2017, in European Application No. 17150114.1.
Burton et al., Rapid Intradermal Delivery of Liquid Formulations Using a Hollow Microstructured Array, Pharmaceutical Research, vol. 28, Issue 1, pp. 31-40, 2011.
Dani et al., High concentration formulation feasibility of human immunoglobulin G for subcutaneous administration, Journal of Pharmaceutical Sciences, vol. 96, No. 6, pp. 1504-1517, 2007.
Ravi et al., Needle free injection technology: a complete insight, International Journal of Pharmaceutical Investigation, vol. 5, No. 4, pp. 192-199, 2015.
Office Action dated Jun. 14, 2018 received in Chilean Application No. 2017-000016.
Office Action issued Jul. 20, 2022 in Taiwanese application No. 106101375.
Li, Guohua, et al. In vitro transdermal delivery of therapeutic antibodies using maltose microneedles. International journal of pharmaceutics, 2009, 109-115.
Bezrodnik, Liliana, et al. Comparative Study of Subcutaneous Versus Intravenous IgG Replacement Therapy in Pediatric Patients with Primary Immunodeficiency Diseases: A Multicenter Study in Argentina. Journal of Clinical Immunology, 2013.
Hagan, John B., et al. Efficacy and safety of a new 20% immunoglobulin preparation for subcutaneous administration, IgPro20, in patients with primary immunodeficiency. Journal of clinical immunology, 2010, 30.5: 734-745.
Product monograph GamaSTAN® S/D. Immune Globulin (Human). 2018.
Vivaglobin®—Product Information-FDA 2006-Package insert approved Jan. 2006.
https://www.rxlist.com/gamunex-drug.htm.
https://www.rxlist.com/rituxan-drug.htm.
https://www.rxlist.com/remicade-drug.htm.
Office Action issued in Brazilian application No. BR102017000820-7 on Dec. 30, 2022.
Office Action issued in Japanese application No. 2014-003151 on Aug. 19, 2021.
Office Action issued in Uruguay application No. 037061 on Sep. 7, 2023.
Geoghegan W.D. The effect of three variables on adsorption of rabbit IgG to colloidal gold. The Journal of Histochemistry and Cytochemistry, 1988, vol. 36(4): 401-407.
Decision to Grant, RU Application No. 2017100665/14, issued Nov. 25, 2021 (English Translation Provided).
Examination Report, RU Application No. 2017100665/14, issued May 7, 2021 (English Translation Provided).
Office Action, RU Application No. 2017100665/14, issued Oct. 9, 2020 (English Translation Provided).
Egorova T.V. Slovar inostrannykh slov sovremennogo russkogo yazyka, Adelant, 2013, p. 338.
Israfilov A.G. 2008. Normal human immunoglobulin. Preparations for intramuscular and subcutaneous administration. Ufa, 2008.
Kuznetsov V.V. Determination of pH. vol. 7, núm. 4, 2001.
Uglova T.A. Subcutaneous administration of immunoglobulin during replacement therapy in childen with primary immunodeficiency. Medical News, 2014, 5, 47-51.

* cited by examiner

INTRADERMAL ADMINISTRATION OF IMMUNOGLOBULIN G PREPARATION

PRIORITY AND CROSS REFERENCE TO RELATED APPLICATIONS

This application is a Continuation Application of co-pending U.S. application Ser. No. 15/407,139, filed on Jan. 16, 2017, which claims the benefit of U.S. Provisional Application 62/292,075, which was filed on Feb. 5, 2016, and which are hereby incorporated by reference in their entireties.

BACKGROUND

Field

The present disclosure is related to a method for administration of IgG preparations by the intradermal (ID) route to a patient in need thereof and a composition for administration of IgG preparations by the ID route to a patient.

Description of the Related Art

Immunoglobulin G (IgG) is the most abundant immunoglobulin isotype in human serum, comprising approximately 80% of all immunoglobulins. IgG preparations are indicated for the treatment of various diseases such as primary immunodeficiency, in particular congenital agammaglobulinaemia and hypogammaglobulinaemia, idiopathic thrombocytopenic purpura, as an adjuvant in the treatment of Kawasaki's Disease and in transplant of bone marrow, hypogammaglobulinaemia associated with chronic lymphocyte leukaemia as part of HIV infection treatment in pediatric patients, among others.

SUMMARY

In some embodiments, a method for administration of an IgG preparation by an intradermal (ID) route to a subject in need thereof is provided, the method comprising loading with a volume of the IgG preparation an ID delivery device comprising needles, applying the device to a skin delivery site, using the device to allow dermal penetration of the needles, delivering the volume of the IgG preparation at the skin delivery site, and removing the delivery device.

In some embodiments of the method, the IgG preparation has an IgG concentration of about 15% to about 30% (w/v). In some embodiments of the method, the IgG preparation has an IgG concentration of about 30% (w/v) or higher.

In some embodiments of the method, a pH of the IgG preparation is about 4.5 to about 8.0. In some embodiments of the method, the pH of the IgG preparation is about 6.5.

In some embodiments of the method, the volume of the IgG preparation is up to about 10 mL per skin delivery site. In some embodiments of the method, the volume of the IgG preparation is between about 2 mL and about 8 mL per skin delivery site. In some embodiments of the method, the volume of the IgG preparation is between about 4 mL and about 6 mL per skin delivery site.

In some embodiments of the method, the IgG preparation comprises one or more additional plasma proteins.

In some embodiments of the method, the subject is a pediatric patient. In some embodiments of the method, the subject is a non-pediatric patient.

In some embodiments, a composition comprising an IgG preparation for treatment of a disease in a subject in need thereof is provided.

In some embodiments of the composition, a concentration of IgG in the IgG preparation is about 15% to about 30% (w/v). In some embodiments of the composition, the concentration of IgG in the IgG preparation is about 30% (w/v) or higher.

In some embodiments, the composition has a pH of about 4.5 and about 8.0. In some embodiments of the composition, the pH is about 6.5.

In some embodiments of the composition, the subject is a pediatric patient. In some embodiments of the composition, the subject is a non-pediatric patient.

In some embodiments of the composition, the disease is an immunodeficiency. In some embodiments of the composition, the immunodeficiency is one of a primary immunodeficiency, a secondary immunodeficiency or an acquired immunodeficiency.

In some embodiments of the composition, the IgG preparation comprises an entire IgG molecule, a therapeutically effective fragment of IgG or a combination thereof.

In some embodiments of the composition, the IgG preparation comprises one or more additional plasma proteins.

BRIEF DESCRIPTION OF THE DRAWINGS

The present disclosure is described below in reference to the following figures.

DETAILED DESCRIPTION

Figure 1:
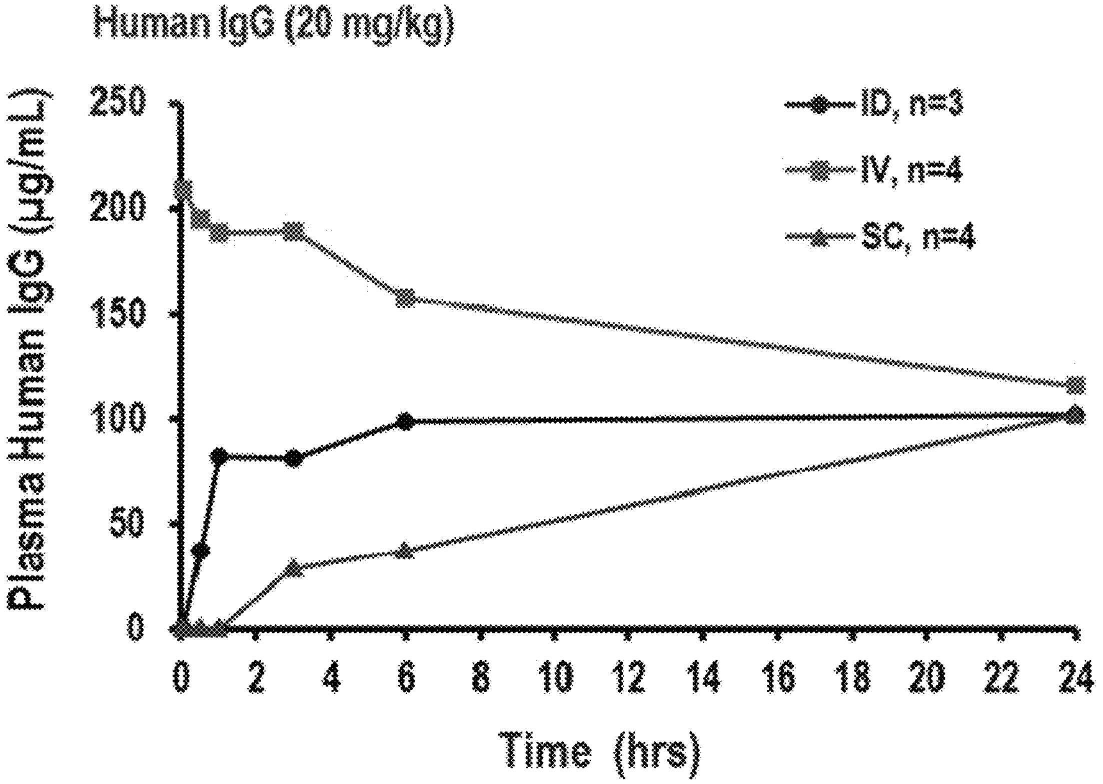
FIG. 1 shows a line graph of plasma human IgG pharmacokinetics at 0-24 h in young farm pigs that were administered an IgG preparation (20 mg/kg) by the IV (n=4), SC (n=4) and ID (n=3) routes.

At present there is high demand for immunoglobulin G (IgG) which is polyvalent with a wide spectrum of human antibodies and has total functionality (neutralizing capacity, opsonization, half-life conserved), with intact molecules (integrity of the crystallizable Fc fragment) and a normal distribution of IgG subclasses identical or equivalent to natural plasma.

The usual routes for the therapeutic administration of IgG preparations include intravenous (IV), subcutaneous (SC) and intramuscular (IM). In addition, IgG may be administered by other routes such as the oral, nasal (inhaled) or topical routes. IV administration has become the standard approach for IgG supplementation in many countries, including the United States.

However, although IV administration offers the most useful therapeutic indications, for example, for the treatment of primary immunodeficiencies or for variable common immunodeficiency (deficit of IgG and IgA subclasses), secondary or acquired immunodeficiencies (for example infection by viruses such as cytomegalovirus, herpes zoster, human immunodeficiency) and diseases of an autoimmune origin (thrombocytopenic purpura, Kawasaki's Syndrome, for example), delivery of plasma-derived protein therapies such as IgG (Immune globulin G) to patients by IV administration route can be associated with infusion-related adverse effects such as flushing, fever, chills and diarrhea. IV infusions also require trained and qualified personnel to administer.

The current primary alternative to IV administration route for patients for IgG is the subcutaneous (SC) route. However, the SC route has been associated with slow progression to peak plasma concentration ($T_{max}$), low plasma area-under-curve (AUC), as well as pain and discomfort.

The intradermal (ID) route, also known as transdermal delivery or percutaneous permeation, is a non-invasive delivery route which is advantageous for the administration of many drugs and/or biologics. ID delivery also overcomes many of the challenges associated with subcutaneous injection by greatly reducing patient discomfort, needle anxiety, risk of accidental needle stick injury to the personnel administering the injection and issues surrounding sharps disposal. In addition, ID systems allow for self-administration, provide sustained release of drugs and/or biologics for periods of time up to one week, and improve patient compliance. Furthermore, ID delivery systems are generally inexpensive.

Despite these many advantages, the ID delivery of drugs is confined to classes of molecules compatible with absorption through the skin. Delivery of therapeutic proteins is not typically viable with traditional ID delivery, as the skin provides an effective protective barrier to these molecules even in the presence of absorption-enhancing excipients. For example, it has been difficult to exploit the ID route to deliver macromolecules.

In addition, although much progress has been made in the development of systems for ID delivery, most commercially available devices that provide ID delivery of liquid formulations remain confined to relatively small volumes, typically less than 200 μL. This makes the intradermal systems not to be considered as a viable alternative for IgG therapy in which grams of proteins have to be administered daily.

However, Burton et al. (Burton S. A. et al., Pharmaceutical Research, Vol. 28, Issue 1, pp. 31-40, (2011)) disclosed intradermal delivery into swine of up to 1.5 mL of a variety of formulations including a polyclonal antibody at a concentration of 57 mg/mL during 5-20 minutes using a microneedle delivery device. The amount of polyclonal antibody delivered with this system (approximately 85 mg) is still very low to be considered as an option for IgG therapy in which, for example, a patient with myositis is typically prescribed with 0.4 to 40 gm/kg over five days, which can be repeated every 4-6 weeks.

The present disclosure provides a method for ID administration of plasma proteins in general and IgG in particular. The method of the present disclosure overcomes the above-mentioned problems and limitations.

Method

The ID route can provide a novel method for allowing self-administration of IgG. Thus, in some embodiments, the present disclosure provides a method for administration of IgG preparations by the ID route. In some embodiments, the method provides for self-administration of IgG preparations by the ID route. In some embodiments, the method provides a superior plasma pharmacokinetic profile of IgG as compared to the SC route. In some embodiments, the method provides a superior plasma pharmacokinetic profile of IgG with a faster $T_{max}$ as compared to the SC route.

In some embodiments, the method provides improved steady state IgG plasma levels due to more frequent dosing regimen, such as a convenient daily injection of IgG. In some embodiments, the method minimizes infusion-related adverse events, such as pain and discomfort related to infusion. In some embodiments, the method improves patient ease of administration and compliance.

In some embodiments, the method for administration of an IgG preparation by intradermal route comprises:

a) loading with a volume of the IgG preparation an ID delivery device comprising needles;
b) applying the device to a skin delivery site;
c) using the device to allow dermal penetration of the needles;
d) delivering the volume of the IgG preparation at the skin delivery site; and
e) removing the delivery device.

In some embodiments, an ID delivery device comprising needles suitable for the method of administration of the present disclosure is provided.

In some embodiments, the skin delivery site is proximal to where treatment is desired. In some embodiments, the skin delivery site is distal to where treatment is desired. In some embodiments, the skin delivery site is where it is convenient to administer a drug. In some embodiments, the skin delivery site is where it is convenient to administer a drug and proximal to where treatment is desired. In some embodiments, the skin delivery site is where it is convenient to administer a drug and distal to where treatment is desired. In some embodiments, the skin delivery site is convenient for self-administration. In some embodiments, the skin delivery site is convenient for drug administration for the person administering a drug.

In some embodiments, the method allows for the administration of a volume of up to about 10 mL per site. In some embodiments, the volume is between about 2 mL and about 8 mL per site. In some embodiments, the volume is between about 4 mL and about 6 mL per site. In some embodiments, the volume is about 0.25, 0.5, 0.75, 1, 2, 3, 4, 5, 6, 7, 8, 9, 10, 11, 12, 13, 14 or 15 mL per site.

In some embodiments, the volume is dependent on the injection solution characteristics. In some embodiments, the volume is dependent on the viscosity of the IgG preparation. In some embodiments, the volume is dependent on the IgG concentration in the IgG preparation. In some embodiments, the volume is dependent on the limitation of the selected ID injection device.

The duration of therapy by the method can vary, without limitation, on the nature of a disease, age of a subject, frequency of administration, dose of IgG preparation, patient compliance, quality and effectiveness of the IgG preparation.

In some embodiments, the duration and frequency of administration depend on, without limitation, the amount of IgG administered, how rapidly the IgG preparation is administered and the pharmacokinetics and pharmacodynamics of the IgG preparation. For example, in some embodiments, the duration of treatment can range from about 1 day to about 28 days. In some embodiments, the duration of treatment can be for about 1, 2, 3, 4, 5, 6, 7, 8, 9, 10, 11, 12, 13, 14, 15, 16, 17, 18, 19, 20, 21, 22, 23, 24, 25, 26, 27 or 28 days. In some embodiments, the duration of treatment can be for about 1 week to about 52 weeks. In some embodiments, the duration of treatment can be for about 5, 6, 7, 8, 9, 10, 11, 12, 13, 14, 15, 16, 17, 18, 19, 20, 21, 22, 23, 24, 25, 26, 27, 28, 29 or 30 weeks. In some embodiments, the duration of treatment is indefinite, for example, the lifetime of a patient. In some embodiments, the frequency of administration is daily. In some embodiments, the frequency of administration is once, twice, thrice or four times daily. In some embodiments, the frequency of administration is daily and the duration of treatment is indefinite. In some embodiments, the frequency of administration is once, twice, thrice or four times daily and the duration of treatment is indefinite.

In some embodiments of the present method, a daily administration regimen would result in more stable plasma concentrations of IgG as compared to IV infusion or SC administration every 3-4 weeks.

In some embodiments, the method comprises using the IgG preparation for the treatment of a disease. In some embodiments, the disease comprises primary immunodeficiency. In some embodiments, the primary immunodeficiency comprises congenital agammaglobulinaemia and hypogammaglobulinaemia and idiopathic thrombocytopenic purpura. In some embodiments, the primary immunodeficiency is a pediatric primary immunodeficiency. In some embodiments, the pediatric primary immunodeficiency is hypogammaglobulinaemia associated with chronic lymphocyte leukaemia. In some embodiments, the pediatric primary immunodeficiency is hypogammaglobulinaemia associated with chronic lymphocyte leukaemia as part of HIV infection treatment in pediatric patients.

In some embodiments, the immunodeficiency is a variable common immunodeficiency. In some embodiments, the variable common immunodeficiency is deficiency of the IgG subclass. In some embodiments, the immunodeficiency is a secondary or acquired immunodeficiency. In some embodiments, the secondary or acquired immunodeficiency is due to infection, for example, by viruses such as cytomegalovirus, herpes zoster virus, human immunodeficiency virus. In some embodiments, the secondary or acquired immunodeficiency is due to a disease of autoimmune origin, for example, thrombocytopenic purpura, Kawasaki's Syndrome. In some embodiments, the IgG preparation can be used as an adjuvant in the treatment of Kawasaki's disease and in bone marrow transplant.

In some embodiments, the method comprises treatment of immunodeficiency in a patient. In some embodiments, the immunodeficiency is primary immunodeficiency. In some embodiments, the immunodeficiency is primary immunodeficiency in a pediatric patient. In some embodiments of the method for treating primary immunodeficiency, the concentration of IgG is about 15% to about 30% (w/v). In some embodiments of the method for treating primary immunodeficiency, the concentration of IgG is about 15, 16, 17, 18, 19, 20, 21, 22, 23, 24, 25, 26, 27, 28, 29 or 30% (w/v). In some embodiments of the method for treating primary immunodeficiency, the concentration of IgG is about 30% (w/v) or higher. In some embodiments of the method, the IgG preparation has a pH of about 4.5 to about 8.0. In some embodiments of the method, the IgG preparation has a pH of about 6.5. In some embodiments of the method, the IgG preparation has a pH of about 4.5, 4.75, 5.0, 5.25, 5.5, 5.75, 6.0, 6.25, 6.5, 6.75, 7.0, 7.25, 7.5, 7.75 or 8.0.

In some embodiments, the age of the subject is from about 10, 15 or 18 years to about 20, 25, 30, 35, 40, 45, 50, 55, 60, 65 or 70 years. In some embodiments, the age of the subject is lower than about 10 years. In some embodiments, the age of the subject is higher than about 70 years. In some embodiments, the method enables treatment of pediatric patients. In some embodiments, the age of the pediatric patient can range from about 1 day to about 18 years. In some embodiments, the sex of the subject is a male. In some embodiments, the sex of the subject is a female.

In some embodiments, the method can be practiced in a hospital, a nursing home, an old age home or a pediatric care facility. In some embodiments, the method can be practiced at home. In some embodiments, the method comprises self-administration, administration by a health care worker or administration by a family member.

In some embodiments, the present disclosure provides a method for the delivery of a therapeutic plasma protein to a patient in need thereof. In some embodiments, the therapeutic plasma protein is an entire IgG. In some embodiments, the therapeutic plasma protein is a therapeutic fragment of an IgG. In some embodiments, the present disclosure provides a method for self-administration of a therapeutic plasma protein. For example, in some embodiments, a patient with a primary immunodeficiency could self-administer a therapeutic plasma protein such as IgG at home rather than going to a clinic for IV administration of the therapeutic plasma protein. The present method provides an administration route that is convenient and less painful as compared to other routes of administration and therefore could lead to greater patient compliance.

Composition

In some embodiments, the composition is an IgG preparation. In some embodiments, the composition is an IgG solution. In some embodiments, the concentration of IgG can be between about 15% and about 30% (w/v). In some embodiments, the concentration is about 7% to about 14%. In some embodiments, the concentration is about 23% to about 30%. In some embodiments, the concentration is about 5, 6, 7, 8, 9, 10, 11, 12, 13, 14, 15, 16, 17, 18, 19, 20, 21, 22, 23, 24, 25, 26, 27, 28, 29 or 30% (w/v). In some embodiments, the concentration is about 30% or higher.

In some embodiments, the composition comprises the entire IgG molecule. In some embodiments, the composition comprises IgG fragments that are therapeutically effective. In some embodiments, the composition can comprise additional antibody types such as IgM, IgA or a combination thereof.

In some embodiments, the composition comprises IgG for the treatment of immunodeficiency in a patient in need thereof. In some embodiments, the composition for treating immunodeficiency has an IgG concentration of about 15% to about 30% (w/v). In some embodiments, the composition for treating immunodeficiency has an IgG concentration of about 30% (w/v) or higher. In some embodiments, the composition for treating immunodeficiency has a pH of about 4.5 to about 8.0. In some embodiments, the composition for treating immunodeficiency has a pH of about 6.5. In some embodiments, the immunodeficiency is primary immunodeficiency. In some embodiments, the immunodeficiency is primary immunodeficiency in a pediatric patient.

In some embodiments, the pH of the IgG solution can be between about 4.5 and about 8.0. In some embodiments, the pH is about 4.5, 4.75, 5.0, 5.25, 5.5, 5.75, 6.0, 6.25, 6.5, 6.75, 7.0, 7.25 7.5, 7.75 or 8.0. In some embodiments, the pH is about 6.5. The pH of the IgG preparation does not cause scabbing of the skin at administration site and is well tolerated.

In some embodiments, the composition is delivered at a skin delivery site that is proximal to where treatment is desired. In some embodiments, the composition is delivered at a skin delivery site that is distal to where treatment is desired. In some embodiments, the skin delivery site is where it is convenient to administer a drug. In some embodiments, the skin delivery site is where it is convenient to administer a drug and proximal to where treatment is desired. In some embodiments, the skin delivery site is where it is convenient to administer a drug and distal to where treatment is desired. In some embodiments, the skin delivery site is convenient for self-administration. In some embodiments, the skin delivery site is convenient for drug administration for the person administering a drug.

In some embodiments, the composition is administered at a volume of up to about 10 mL per site. In some embodiments, the volume is between about 2 mL and about 8 mL per site. In some embodiments, the volume is between about 4 mL and about 6 mL per site. In some embodiments, the volume is about 0.25, 0.5, 0.75, 1, 2, 3, 4, 5, 6, 7, 8, 9, 10, 11, 12, 13, 14 or 15 mL per site.

In some embodiments, the volume is dependent on the injection solution characteristics. In some embodiments, the volume is dependent on the viscosity of the IgG preparation. In some embodiments, the volume is dependent on the IgG concentration in the IgG preparation. In some embodiments, the volume is dependent on the limitation of the selected ID injection device.

In some embodiments, the duration and frequency of administration of the composition depend on, without limitation, the amount of IgG administered, how rapidly the IgG preparation is administered and the pharmacokinetics and pharmacodynamics of the IgG preparation. For example, in some embodiments, the duration of treatment can range from about 1 day to about 28 days. In some embodiments, the duration of treatment can be for about 1, 2, 3, 4, 5, 6, 7, 8, 9, 10, 11, 12, 13, 14, 15, 16, 17, 18, 19, 20, 21, 22, 23, 24, 25, 26, 27 or 28 days. In some embodiments, the duration of treatment can be for about 1 week to about 52 weeks. In some embodiments, the duration of treatment can be for about 5, 6, 7, 8, 9, 10, 11, 12, 13, 14, 15, 16, 17, 18, 19, 20, 21, 22, 23, 24, 25, 26, 27, 28, 29 or 30 weeks. In some embodiments, the duration of treatment is indefinite, for example, the lifetime of a patient. In some embodiments, the frequency of administration is daily. In some embodiments, the frequency of administration is once, twice, thrice or four times daily. In some embodiments, the frequency of administration is daily and the duration of treatment is indefinite. In some embodiments, the frequency of administration is once, twice, thrice or four times daily and the duration of treatment is indefinite.

In some embodiments, the composition comprises an IgG preparation for the treatment of a disease. In some embodiments, the disease comprises primary immunodeficiency. In some embodiments, the primary immunodeficiency comprises congenital agammaglobulinaemia and hypogammaglobulinaemia and idiopathic thrombocytopenic purpura. In some embodiments, the primary immunodeficiency is a pediatric primary immunodeficiency. In some embodiments, the pediatric primary immunodeficiency is hypogammaglobulinaemia associated with chronic lymphocyte leukaemia. In some embodiments, the pediatric primary immunodeficiency is hypogammaglobulinaemia associated with chronic lymphocyte leukaemia as part of HIV infection treatment in pediatric patients.

In some embodiments, the immunodeficiency is a variable common immunodeficiency. In some embodiments, the variable common immunodeficiency is deficiency of the IgG subclass. In some embodiments, the immunodeficiency is a secondary or acquired immunodeficiency. In some embodiments, the secondary or acquired immunodeficiency is due to infection, for example, by viruses such as cytomegalovirus, herpes zoster virus, human immunodeficiency virus. In some embodiments, the secondary or acquired immunodeficiency is due to a disease of autoimmune origin, for example, thrombocytopenic purpura, Kawasaki's Syndrome. In some embodiments, the IgG preparation can be used as an adjuvant in the treatment of Kawasaki's disease and in bone marrow transplant.

In some embodiments, the composition comprises treatment of immunodeficiency in a patient. In some embodiments, the immunodeficiency is primary immunodeficiency. In some embodiments, the immunodeficiency is primary immunodeficiency in a pediatric patient. In some embodiments, the composition is for treating primary immunodeficiency, the concentration of IgG is about 15% to about 22% (w/v). In some embodiments, the composition is for treating primary immunodeficiency, the concentration of IgG is about 15, 16, 17, 18, 19, 20, 21, 22, 23, 24, 25, 26, 27, 28, 29 or 30% (w/v). In some embodiments of the composition for treating primary immunodeficiency, the concentration of IgG is about 30% (w/v) or higher. In some embodiments of the composition, the IgG preparation has a pH of about 4.5 to about 8.0. In some embodiments of the composition, the IgG preparation has a pH of about 6.5. In some embodiments of the composition, the IgG preparation has a pH of about 4.5, 4.75, 5.0, 5.25, 5.5, 5.75, 6.0, 6.25, 6.5, 6.75, 7.0, 7.25, 7.5, 7.75 or 8.0.

In some embodiments, the age of the subject is from about 18 years to about 70 years. The age of the subject may be 10, 15, 20, 25, 30, 35, 40, 45, 50, 55, 60, 65 or 70 years. In some embodiments, the age of the subject is lower than about 18 years. In some embodiments, the age of the subject is higher than about 70 years. In some embodiments, the composition enables treatment of pediatric patients. In some embodiments, the age of the pediatric patient can range from about 1 day to about 18 years. In some embodiments, the sex of the subject is a male. In some embodiments, the sex of the subject is a female.

In some embodiments, the composition can be administered in a hospital, a nursing home, an old age home or a pediatric care facility. In some embodiments, the composition can be administered at home. In some embodiments, the composition can be self-administered, administered by a health care worker or administered by a family member.

EXAMPLES

Example 1. Administration of an IgG Preparation to Pigs Via IV, SC and ID

Young farm pigs (20-25 kg) were administered with IgG (20 mg/kg) by the IV (n=4), SC (n=4) and ID (n=3) routes. Venous blood samples were obtained at 2, 30 and 60 min; 3 and 6 hours and then daily for 10 days after IgG administration for measurement of human-specific IgG by immunoassay.

Figure 2:
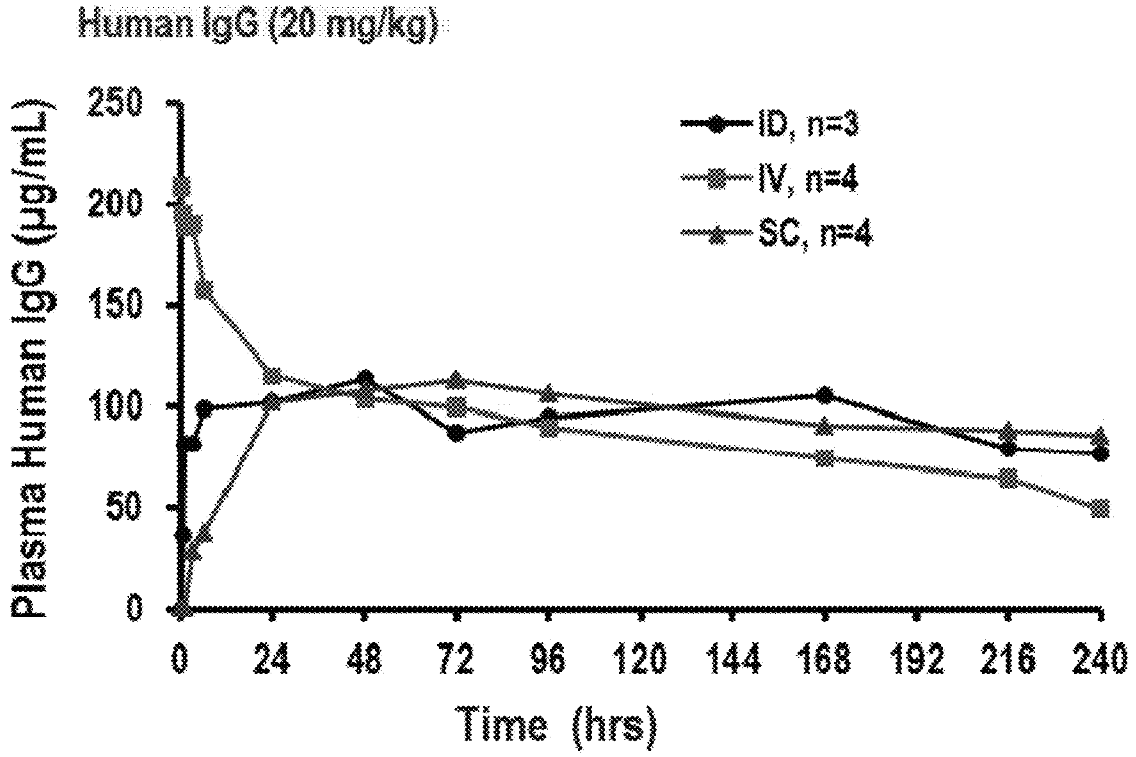
FIG. 2 shows a line graph of plasma human IgG pharmacokinetics at 0-240 h in young farm pigs that were administered an IgG preparation (20 mg/kg) by the IV (n=4), SC (n=4) and ID (n=3) routes

As shown in FIG. 1, the ID route had faster uptake of IgG into the plasma compartment as compared to the SC route. The plasma concentration of IgG approached $C_{max}$ within 1 hour after administration by the ID route, whereas $C_{max}$ for the SC route was not achieved for 24 hours. FIG. 1 and FIG. 2 show the time course of plasma IgG after administration by IV, ID and SC routes. The same plasma pharmacokinetic data are shown 0-24 hours (FIG. 1) as well as on a compressed X-axis over 10 days (FIG. 2). Clearly, 24 hours onwards in this experimental model, the plasma levels of IgG are similar irrespective of the route of administration. Thus, the elimination half-life (T½) for all three routes is very similar.

Example 2. Influence of IgG Preparation pH on the Delivery Site

To evaluate the influence of the IgG preparation pH on the delivery site, 2 mL of Gamunex® and IGSC 20% IgG formulations (Grifols Therapeuctics Inc., USA) both at pH 4.0, and IGIM-S/D (Grifols Therapeuctics Inc., USA) at pH 6.5, were administered to young farm pigs.

Three days following 2 mL administration of IgG, the low pH administration causes scabbing of the skin at administration site whereas neutral pH IgG appears to have good tolerability.

Example 3. Pediatric Treatment

The method according to the present disclosure can be used for treating a pediatric patient with a primary immunodeficiency. The weight of the patient is about 25 kg. The typical dose range for such a patient is about 300 to about 800 mg/kg body weight over about 4 weeks. This does can be achieved using the present method with one ID administration of about 2 mL or about 4 mL of a concentrated IgG preparation. The concentrated IgG preparation has a concentration of IgG of about 16.5% or about 20% (w/v).

What is claimed is:

1. A method for treating a disease selected from the group consisting of an immunodeficiency, a disease of autoimmune origin, or combinations thereof in a subject in need thereof, the method comprising:

administering a pooled human plasma-derived intravenous IgG antibody solution further comprising IgA and IgM to the subject using an ID delivery device comprising needles, wherein the ID delivery device is applied to a skin delivery site to allow dermal penetration of the needles such that the pooled human plasma-derived intravenous IgG antibody solution further comprising IgA and IgM is delivered at the skin delivery site, wherein the pooled human plasma-derived IVIG antibody preparation is about 2 mL to about 8 mL in volume with a pH of about 6.5, and has IgG concentration of about 16.5% to about 20% (w/v).

2. The method according to claim 1, wherein the subject is a pediatric patient.

3. The method according to claim 1, wherein the subject is a non-pediatric patient.

4. The method according to claim 1, wherein the immunodeficiency is one of a primary immunodeficiency, a secondary immunodeficiency or an acquired immunodeficiency.

* * * * *